United States Patent
Hemker et al.

(10) Patent No.: US 8,828,730 B2
(45) Date of Patent: Sep. 9, 2014

(54) METHOD AND ASSEMBLY FOR MEASURING THROMBIN GENERATION IN PLASMA

(75) Inventors: Hendrik Coenraad Hemker, Maastricht (NL); Rafael Jesus Apitz-Castro, Maastricht (NL); Sebastiaan Nijhuis, Maastricht (NL)

(73) Assignee: Synapse B.V., Maastricht (NL)

( * ) Notice: Subject to any disclaimer, the term of this patent is extended or adjusted under 35 U.S.C. 154(b) by 29 days.

(21) Appl. No.: 13/057,898

(22) PCT Filed: Aug. 5, 2009

(86) PCT No.: PCT/NL2009/050480
§ 371 (c)(1),
(2), (4) Date: Apr. 27, 2011

(87) PCT Pub. No.: WO2010/016762
PCT Pub. Date: Feb. 11, 2010

(65) Prior Publication Data
US 2011/0195441 A1 Aug. 11, 2011

Related U.S. Application Data

(60) Provisional application No. 61/086,210, filed on Aug. 5, 2008.

(30) Foreign Application Priority Data

Aug. 5, 2008 (EP) .................................... 08161848

(51) Int. Cl.
*G01N 33/543* (2006.01)
(52) U.S. Cl.
USPC ............... 436/66; 436/518; 436/520; 436/43; 436/16; 436/164; 436/165; 436/169; 436/177; 435/288.7; 435/283.1; 435/287.1; 435/287.7; 435/288.6; 422/400; 422/401; 422/402; 422/403; 422/404; 422/420; 422/82.05; 422/502; 422/503

(58) Field of Classification Search
USPC ......... 422/400–404, 420–422, 502–503, 507, 422/82.05, 82.07–82.08; 436/518, 520, 43, 436/66, 164, 165, 172, 177, 180, 14, 16, 436/169; 435/5, 283.1, 287.1, 287.7, 288.6, 435/288.7
See application file for complete search history.

(56) References Cited

U.S. PATENT DOCUMENTS

| | | | | |
|---|---|---|---|---|
| 5,418,143 | A | * | 5/1995 | Zweig .............................. 435/13 |
| 6,395,501 | B1 | * | 5/2002 | Rosen et al. ..................... 435/13 |
| 6,518,068 | B1 | * | 2/2003 | Gambini et al. ................ 436/50 |
| 6,730,490 | B2 | * | 5/2004 | Rosen et al. .................... 435/13 |

(Continued)

FOREIGN PATENT DOCUMENTS

EP       1717588 A1   11/2006
WO   WO 2007089777 A2   8/2007

*Primary Examiner* — Brian R Gordon
(74) *Attorney, Agent, or Firm* — Browdy and Neimark, PLLC

(57) ABSTRACT

Disclosed is a method for measuring thrombin generation in a whole blood sample. The whole blood sample may be applied forthwith, without prior processing. The blood cells and blood plasma in the whole blood sample are separated by (lateral) flow migration. Also disclosed is an assembly of a sample support and a device dedicated to measure thrombin generation in a whole blood sample. Advantageously, the sample support comprises a separator medium allowing separation of whole blood into blood cells and blood plasma by means of (lateral) flow migration.

16 Claims, 3 Drawing Sheets

(56) References Cited

U.S. PATENT DOCUMENTS

Figure 1A:
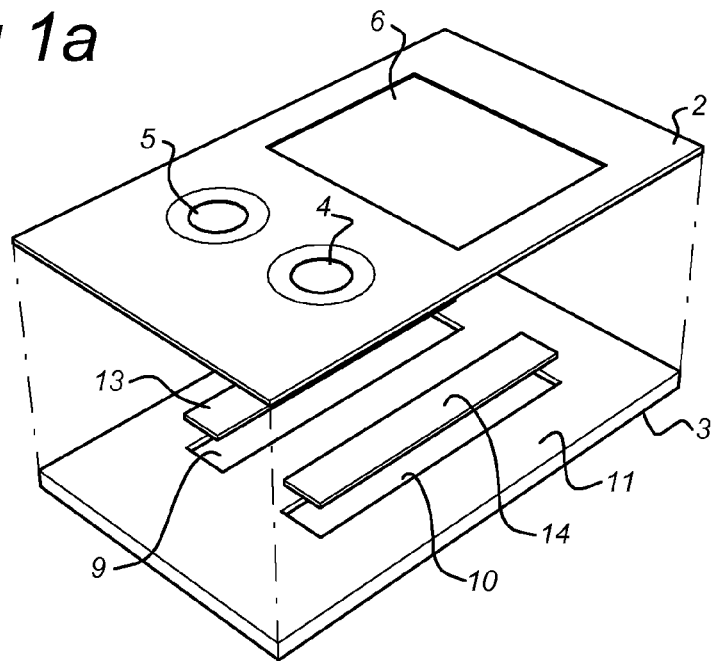

| | | |
|---|---|---|
| 6,800,450 B2 * | 10/2004 | Rosen et al. .................. 435/13 |
| 7,118,880 B2 * | 10/2006 | Rosen et al. .................. 435/13 |
| 2002/0114734 A1 | 8/2002 | Pantoliano et al. |
| 2004/0235078 A1 * | 11/2004 | Rosen et al. .................. 435/13 |
| 2007/0275420 A1 * | 11/2007 | Ohyama et al. ............. 435/7.23 |
| 2009/0311730 A1 * | 12/2009 | Hemker et al. ................ 435/13 |
| 2010/0279423 A1 * | 11/2010 | Brennan et al. ................ 436/94 |
| 2011/0236879 A1 * | 9/2011 | Egan et al. ....................... 435/5 |

* cited by examiner

METHOD AND ASSEMBLY FOR MEASURING THROMBIN GENERATION IN PLASMA

FIELD OF THE INVENTION

The present invention relates to a simple method to measure thrombin generation in plasma without the need for a previous step of centrifugation of a whole blood sample. It also relates to the design and use of a dedicated equipment for the measurement of the thrombin generation and the estimation of parameters that characterize the generation of thrombin in blood plasma.

BACKGROUND OF THE INVENTION

Coagulation and fibrinolysis are two apparently independent processes which together constitute the haemostatic system of the blood. This system is responsible for, on one side, keeping the free-flow of blood through the blood vessels and on the other side preventing excessive blood loss following a wound. The enzyme thrombin [EC 3.4.21.5] plays a pivotal role in both situations and, indeed is the most important link between both processes. Thrombin production is a complex event that includes generation of active thrombin from precursors as well as inactivation of the formed thrombin by physiological inhibitors. Further, thrombin itself promotes its own formation and inactivation. It has become clear that measuring the progress of thrombin activity in time (thrombin generation) results in a global appraisal of the haemostatic system (1, 2).

The necessity to measure the function of the haemostatic system has not escaped the attention of the medical profession over the last century. Since the 50ies, it has been recognized that measuring the time course of thrombin in clotting blood gave the best estimate of the functionality of the haemostatic system, as well as of the propensity towards thrombotic or bleeding states. From the eighties on, fundamental work from HC Hemker's laboratory in Maastricht resulted in the development of a computerized, automatic method that allows estimation of the thrombin generation parameters with relatively high output, from Platelet-free (PPP) as well as Platelet-rich plasma (PRP) [EP-B2-0420332 and WO 03/093831A1]. Following the basic principles of Hemker's development, other groups have implemented alternative methods to measure thrombin generation in plasma which, due to the lack of appropriate calibration [WO 03/093831 A1], give variable and imprecise estimates of the thrombin generation parameters [[1,2]].

Up to this date, all the existing methods for measuring thrombin generation in plasma need an additional, non-automatic step, previous to the actual measurement. That is, in order to obtain PPP or PRP the sample of whole blood have to be subjected to centrifugation in order to separate the cellular components of the blood from the plasma. Besides the obvious extra manipulation of the sample, this step, by depleting the sample from cells, will not allow the estimation of their contribution to the generation of thrombin.

The present invention provides a method by which triggering of thrombin generation will be done in a sample of whole blood, while the actual measurement of the progress of thrombin activity in time will be followed in plasma, in a single step, without the need for a previous separation of the blood cells.

SUMMARY OF THE INVENTION

In an aspect, the present invention relates to an assembly of a sample support and a device for measuring thrombin generation in plasma, the device comprising a housing having a light tight box having a cartridge retainer received therein and wherein at least a part of a light source and a part of a light sensor are directed towards said cartridge retainer, said light tight box having a insertion opening for inserting the sample support and for directing the sample support into a receiving space for the sample holder in the cartridge retainer, wherein the sample support comprises a longitudinal separator medium having a sampling area near one end of the separator medium and a reading area near the other end, said other end being receivable in the insertion opening and the receiving space.

In a further aspect, the invention is concerned with a method for measuring thrombin generation in a whole blood sample. The method comprises the steps of: a) separating the blood cells from the blood plasma by means of flow migration, preferably lateral flow migration, of blood plasma with retention of blood cells immediately after induction of thrombin generation, and b) measuring thrombin generation in the blood plasma. The inventive method avoids the need of a centrifugation step of whole blood prior to measurement of thrombin generation.

DESCRIPTION OF THE DRAWINGS AND FIGURES

Figure 1B:
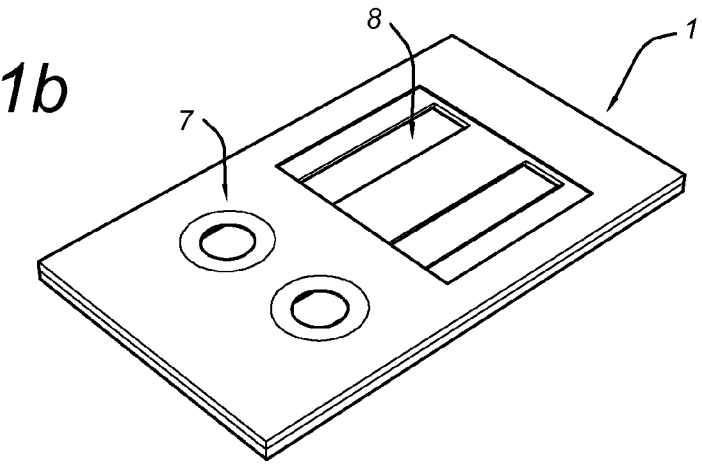
Figure 2:
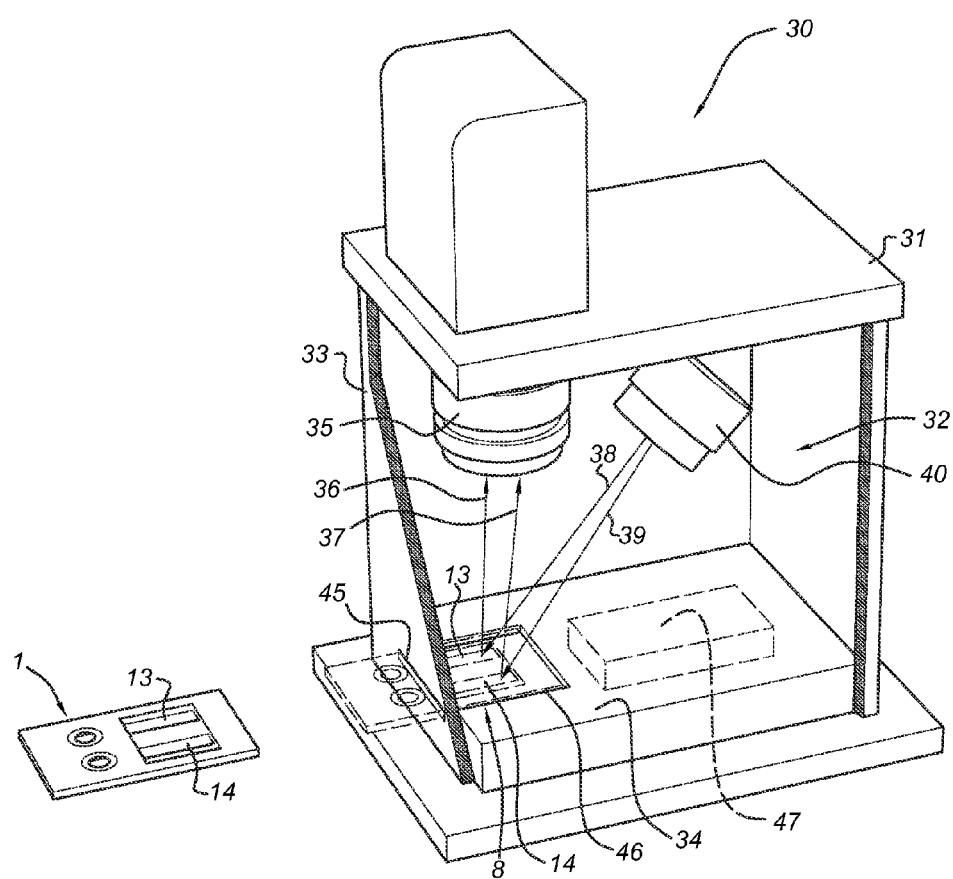
Figure 3:
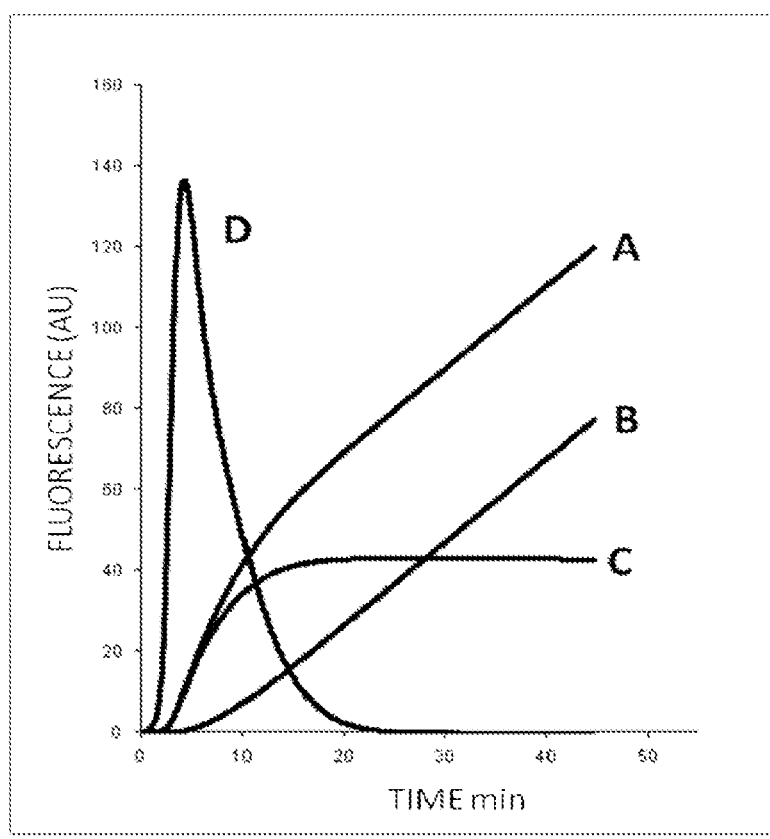

The invention will be further elucidated hereinafter referring to the following drawings and figures, wherein FIGS. 1a and 1b show perspective views of first embodiment of a sample support, FIG. 2 shows a perspective, partly exploded view of an embodiment of the assembly according to the invention, FIG. 3 shows the progress curve [A] for the apparition of the product, after correcting for substrate consumption (inner filter effect, if present at all, is negligible due to the measurement being done in a thin layer). The actual curve for the activity of free thrombin is shown in [C], and obtained from subtracting the activity due to the α2M-thrombin complex [B] from the total activity [A]. The first derivative of [C], shown in [D], represents the well known course of thrombin generation in plasma. The curve in [C] may be converted to Thrombin units using the initial rate and known activity of a calibrator. This external calibration can be done before, in parallel, or after assaying the experimental sample. Calculation of other parameters of the thrombin generation process like the Endogenous Thrombin Potential (ETP) can be done by the use of mathematical procedures known to any skilled operator [6].

DETAILED DESCRIPTION OF THE INVENTION

Whole blood is composed of blood cells, e.g. white and red blood cells, and blood plasma. Hitherto, thrombin generation in blood was measured in blood plasma after centrifugation of whole blood to separate the blood cells from the blood plasma. The present invention now provides a method for measuring thrombin generation in a whole blood sample, wherein the blood cells are separated from the blood plasma by means of flow migration, preferably lateral flow migration, of blood plasma with retention of blood cells immediately after induction of thrombin generation. In the inventive method separation of whole blood by means of centrifugation is not required. Generally, thrombin generation is triggered in a blood sample in the presence of a fluorogenic thrombin-substrate, according to procedures known in the art. Thrombin generation will eventually be measured in the blood plasma thus separated from the blood cells.

In an embodiment, a whole blood sample is applied onto a sample support comprising a separator medium allowing for flow migration, preferably lateral flow migration, of blood plasma with retention of blood cells, preferably a longitudinal separator medium. The whole blood may then be applied near one end of the separator medium. In an advantageous embodiment, the flow migration is caused by capillary properties of the separator medium. Due to the capillarity, blood plasma will migrate through the separator medium considerably faster than blood cells, such that these blood components are separated. Due to the capillary separation, part of the separator medium will contain blood plasma without blood cells. In an embodiment, the flow migration herein referred to takes place in the lateral direction. Thrombin generation may subsequently be measured in the blood plasma in accordance with methods well-known in the art, such as monitoring of fluorescence intensity. Moreover, the development and disappearance of the thrombin in the plasma from said measured fluorescence can be derived.

The term "a whole blood sample" as herein used refers to a mixture of whole, anticoagulated blood either undiluted or admixed with one or more components used for measurement of thrombin generation. In an embodiment, the components used for measurement of thrombin generation are previously incorporated in a separator medium, as will be further illustrated herein below. The components used for measurement of thrombin generation are generally substances that govern the way in which thrombin is generated such as phospholipids, tissue factor, contact activator, thrombomodulin or activated protein C (APC) in a suitable buffer, or any other suitable reagent that may be used for the development of thrombin generation according to a preferred pathway. Furthermore, any other additional component of which one wishes to know its effect on thrombin generation (i.e. a potential antithrombotic drug) may be added.

Thrombin generation is generally triggered with a solution of a $Ca^{++}$ salt so as to obtain the appropriate final concentration. A fluorogenic thrombin substrate, which is useful for probing the thrombin formed, may be added together with the other components before triggering with the $Ca^{++}$ solution or together with the $Ca^{++}$ solution. [3]. The final volume of the reaction mixture is irrelevant (but is preferably about 120 μL), provided that the appropriate final concentration of all the components is maintained. As with all known methods for measuring the parameters of the thrombin generation curve, appropriate calibration is also needed [3]. In the present invention, the calibrator can be measured before, in parallel or after the acquisition of the thrombin generation curve.

Alternatively, appropriate amounts of Ca-salt, fluorogenic substrate and/or other components, as mentioned above, may be previously applied to the separator medium and dried, so that the desired concentrations are achieved as soon as the whole blood sample penetrates the separator medium.

Preferably, the separator medium is made of cellulose or a cellulose derivative. In an embodiment, the separator medium ensures lateral separation of blood plasma from blood cells by means of capillary electrophoresis. The separator medium may advantageously be a membrane type FR-2 (0.7), commercially available from Advanced Microdevices PVT. LTD, Ambala, India.

In an embodiment, the separator medium further comprises one or more reagents for measuring thrombin generation, such as the components for measuring thrombin generation referred to hereinabove. In case the separator medium comprises all components required for inducing and measuring thrombin generation, the whole blood sample may be applied to the sampling area of the sample support forthwith.

The separator medium may also comprise one or more, but not all, components for inducing and measuring thrombin generation. In such case, the whole blood sample is to be admixed with the remaining components necessary for inducing and measuring thrombin generation. Alternatively, the separator medium may not comprise any components necessary for inducing and measuring thrombin generation, in which case all components will have to be admixed with the whole blood sample. Evidently, after addition of the component inducing thrombin generation, preferably $Ca^{++}$, the whole blood sample will have to be applied onto the separator medium immediately in order for thrombin generation to be measured.

In an embodiment, the separator medium is received in a body of the sample support and the sample are and the reading area are openings in the body of the sample support. The separator medium may be received in between two separable body parts of the sample support.

The present invention also provides for an assembly of a sample support and a device for measuring thrombin generation in plasma, the device comprising a housing having a light tight box having a cartridge retainer received therein and wherein at least a part of a light source and a part of a light sensor are directed towards said cartridge retainer, said light tight box having a insertion opening for inserting the sample support and for directing the sample support into a receiving space for the sample holder in the cartridge retainer, wherein the sample support comprises a longitudinal separator medium having a sampling area near one end of the separator medium and a reading area near the other end, said other end being receivable in the insertion opening and the receiving space. The assembly is particularly suited for measuring thrombin generation in a whole blood sample. The sample support advantageously has the properties as described hereinabove.

The assembly of the present invention allows for applying the whole blood sample outside a light-tight measurement compartment whereas detection, e.g. fluorescence detection, takes place on the part of the separating support containing only the blood plasma part of whole blood (reading area).

In an embodiment, e.g. in case of aminomethylcoumarine being the fluorescent product to be measured in the reading area of the sample support, the light source is arranged for emitting light with a spectral from 350-400 nm and the light sensor is a camera comprising a cut-off filter with spectral range from 400 to 430 nm.

The device may further advantageously comprise a heating block for maintaining a temperature in the range of about 34° C. to about 40° C., preferably about 37° C. to about 38° C., more preferably about 37.4° C. to about 37.6° C.

The blood cells are preferably separated from the blood plasma in a sample support as defined hereinabove, and in an assembly as defined hereinabove.

Once thrombin generation is triggered in the whole blood sample, a volume ranging from about 25 to about 200 μL, preferably about 80 μL, thereof may be deposited on the sampling area enclosed in a cartridge, e.g. made of plastic. The separator medium must have the property that blood plasma travels faster than blood cells. Lateral separation of the blood plasma from the blood cells preferably takes about 5-15 seconds, more preferably about 10 seconds. Thrombin generation is then monitored on the reading area. In the reading area no blood cells but only blood plasma (and the other components of the whole blood sample) has moved. In the reading area thrombin generation is detected, e.g. by measuring the increase of fluorescence intensity caused by the product of enzymatic cleavage of a fluorogenic substrate. The separator medium may be (but not restricted to) any means allows a rapid separation of the cellular components of the blood from the blood plasma once thrombin generation have been triggered, centrifugation being excepted. A preferred separator medium is the membrane type FR-2(0.7) from Advanced Microdevices PVT. LTD, Ambala, India. By the action of the formed thrombin, the fluorogenic substrate may be cleaved yielding as one of the products a fluorophore, which under excitation by light of the appropriate wavelength will emit light at a higher wavelength. Fluorogenic substrates as herein used refers to substrates comprising a peptide sequence susceptible of cleavage by thrombin, i.e. peptide sequences having the structure AA-Arg-R (AA being any amino acid, R being the fluorophore). In an embodiment, fluorescent substrates for measuring thrombin generation comprise aminomethylcoumarine as fluorophore. In another embodiment, Rhodamine-110 may be the fluorophore. A non-limiting example of a commercially available substrate that may be used for measuring thrombin generation is (p-to-syl-Gly-Pro-Arg)$_2$-Rho110 (Molecular Probes Inc., Oregon, USA, Cat.# R22124).

The change of intensity of the emitted light as a function of time may be followed by means of any light-sensitive device, i.e. (but not restricted to) photodiodes, photomultipliers, photon detection units, and CCD sensors (preferably a monochrome CCD Firewire camera fitted with a variable focus and aperture lens). Cameras can be connected to a desktop or laptop computer via a framegrabber, USB port or firewire port. Data acquisition can be done through the use of dedicated software while data processing can be performed either through a dedicated software or manually in a spreadsheet in order to obtain the parameters of the thrombin generation curve.

The device according to the present invention may suitably comprise the following components: a heating block for maintaining the temperature of the thrombin generation reaction at the desired temperature; a sample support and cartridge which contains the separator medium; a light source, e.g. consisting of (but not restricted to) 1 to 15 Light Emitting Diodes (LEDs) with a spectral range from 360 to 390 nm (preferably with emission maximum at 380 nm); the geometry of the light source can be a lineal, square or preferably a circular array of LEDs; a band pass filter with a spectral range from 350 to 400 nm, suitable in case the signalling group split off by thrombin (i.e. generated by thrombin and to be detected) is aminomethylcoumarine; other filters may be needed with other signalling groups; a diffuser to achieve homogeneous light distribution from the light source; a light sensor, such as (preferably but not restricted to) a CCD black&white Firewire camera fitted with a lens f=8 mm F=1.4) to which a cut-off filter, e.g. with spectral range from 400 to 430 nm, is attached, which is suitable in case the signalling group split off by thrombin is aminomethylcoumarine; a cut-off filter with spectral range from 500+/−5 nm and camera filter with spectral range of 530+/−10 nm may be suitable for rhodamine-110 comprising substrates; other filters may be needed with other signalling groups. The light source and the sensor lens are preferably encased in an appropriate light-tight box. The camera body may be located outside the box. The sample support is preferably located half inside, half outside the measuring chamber. The blood may then be applied on the part outside the light-tight box, whereas the thrombin generation measurement may be carried out inside the light tight box.

It is to be noted that thrombin generation in Platelet Poor Plasma (PPP) and/or any other media containing cells and/or particulate material may be similarly measured using the method and assembly of the present invention.

The invention will hereinafter be illustrated by reference to the appended drawings and figures, and the examples. It is to be understood that these are incorporated merely to illustrate the invention, and not to limit the invention in any way.

FIGS. 1a and 1b show a first embodiment of a sample support 1 according to an embodiment of the invention. It is an example of a sample support to be used in combination with an assembly according to an aspect of the invention. According to this embodiment the sample support 1 or cartridge 1 comprises two support parts 2,3 which can be assembled to form a body for the sample support 1.

Part 2 comprises a rectangular body having three openings 4-6. Openings 4,5 form two openings for depositing a sample. Openings 4,5 form the sampling area 7. Opening 6 comprises an opening for performing an experiment/measurement and forms the reading area 8 of the sample support 1.

Part 3 comprises two longitudinal grooves 9,10 on an inside surface area 11 that faces the inside surface area of part 2 when the two parts 2,3 are assembled. In the grooves a suitable longitudinal separator medium can be received. The separator medium can be (but not restricted to) any means not involving centrifugation that allows a rapid separation of cellular components of blood from the plasma. In an embodiment the separator medium is the membrane type FR-2(0.7) from Advanced Microdevices PVT. LTD, Ambala, India.

In the shown embodiment the separator medium comprises two strips 12,13 that have a shape and thickness corresponding to the grooves 9,10. The invention is not limited to a certain shape of the separator medium.

Parts 2 and 3 can be assembled to form the sample support 1 as shown in FIG. 1b. It is possible to disassemble the sample support 1. The inside surface areas 11 of the two parts 2,3 can be releasable connected to each other. The skilled person is able to form a suitable connection means on the parts 2,3 to connect the parts to each other.

In the assembled state as shown in FIG. 1b, two blood samples can be deposited onto the separator medium 12,13 through the openings 4,5 in the sample area 7.

In an embodiment a drop of the mixture of the blood with or without admixed reactants is placed on the medium 12,13. The red blood cells will travel much slower than the plasma. In an embodiment an appropriate virtually bi-dimensional support is used. The reading area 8 will have a portion of the plasma without red blood cells.

The volume of sample placed on the medium 12,13 can range from 10 to 400 μL, in an embodiment 25 to 200 μL and in a specific embodiment 80 μL. The sample is deposited on the strip of the separator media (in an embodiment the size is 5 mm wide×30 mm length) enclosed in a plastic sample support. The separator media must have the property that plasma travels faster than red blood cells. Lateral separation of the plasma from the cell components of the blood takes about 10 seconds.

The assembled sample support 1 has an envelope like structure. This allows the support structure to be received in a suitable retainer.

An embodiment according to FIGS. 1a, 1b can used in a method for measuring thrombin generation. Thrombin generation is triggered in a blood sample in the presence of a fluorogenic thrombin-substrate, according to procedures known to the art. The configuration of the support structure 1 allows to apply the sample, in an embodiment blood, outside a light-tight measurement compartment whereas fluorescence-detection takes place on the plasma containing part of the support located within that compartment.

This allows to monitor the fluorescence intensity in the plasma and to derive the development and disappearance of the thrombin in the plasma from said measured fluorescence. In an embodiment the sample consists of a mixture of whole, anticoagulated blood either undiluted or admixed with the required reactants but without the $Ca^{++}$ ions that trigger thrombin generation process. When undiluted, fresh blood is used forthwith, the required reaction components are previously incorporated in the separator strip. In an embodiment the components, besides whole blood, are substances that govern the way in which thrombin is generated such as phospholipids, tissue factor, contact activator, thrombomodulin or activated protein C (APC) in a suitable buffer, or any other suitable reagent that may be required for the development of thrombin generation according to an embodiment. Furthermore any other additional component of which one wishes to know its effect on thrombin generation (i.e. a potential antithrombotic drug). Thrombin generation is triggered with a solution of a $Ca^{++}$ salt so as to obtain the appropriate final concentration. The fluorogenic thrombin substrate, which is essential for probing the thrombin formed may be added together with the other components before triggering with the $Ca^{++}$ solution or together with the $Ca^{++}$ solution.

The final volume of the reaction is irrelevant (in an embodiment 120 µL), provided that the appropriate final concentration of all the components is maintained. As with all known methods for measuring the parameters of the thrombin generation curve, appropriate calibration is also needed. In the present invention, the calibrator can be measured before, in parallel or after the acquisition of the thrombin generation curve. Thrombin generation is then monitored on the area, here the reading area 6, where only plasma (and the other components of the reaction) has moved by measuring the increase of fluorescence intensity caused by the product of the enzymatic cleavage of the fluorogenic substrate.

In an embodiment an assembly for measuring fluorescent parameters of a sample is provided comprising the support structure 1 according to FIGS. 1a and 1b and further comprising a device 30. The device 30 according to an embodiment is arranged for measuring thrombin generation in plasma. The device 30 can comprise a housing 31 having a light tight box 32. Within the housing light sensitive experiments or measuring methods can be performed.

FIG. 2 shows an example embodiment of such a device 30. The view is partly exploded as part of the front wall 33 is removed. This allows a view of the interior space 32 of the device.

The device can have a cartridge retainer 34, here formed by bottom part 34 of the light tight box 32. The retainer can be part of the housing. The retainer 34 can be used to hold or receive a support 1 that holds the sample.

In order to measure at least one parameter of the sample at least a radiation sensor 35, in an embodiment a light sensor 35, is directed towards said cartridge retainer 34. This will allow the radiation sensor 35 to sense and measure at least one parameter of the radiation 36,37 emitted from the sample in particular from the sample on the two strips 13,12 of separating medium received in the reading area 8 of the sample support 1. The radiation sensor 35 has at least one input channel that is in open connection with the light tight box 32 in which the sample is received. This will allow an undisturbed measurement. In the embodiment according to FIG. 2 most of the camera 35 is received in the light tight box 32.

In an embodiment the light sensor 35 is a camera, in a particular embodiment a CCD black&white firewire camera fitted with a lens f=8 mm F=1.4. In an embodiment the camera 35 comprises a cut off filter with spectral range from 400 to 430 nm. This is a range of light which is especially suited for fluorescence measurements.

A cut-off filter with spectral range from 400 to 430 nm can be attached to the camera 35 or is at least positioned upstream from the camera in the pathway 36,37 of the radiation emitted by the sample. Such filter is advantageous when the signalling group split of by thrombin is aminomethylcoumarine. Other filters may be needed with other signalling groups.

In an embodiment the device 30 also comprises a radiation source 40, in an embodiment a light source. The radiation source can provide radiation at a specific wavelength (range). This will allow conducting an experiment in order to obtain the suitable measurement parameters with the radiation sensor. Rays of radiation 38,39 are emitted onto the sample 12,13.

In an embodiment the light source 40 and light sensor 35 are arranged to conduct a fluorescence experiment. In embodiment the light source 40 is arranged for emitting light with a spectral from 350-400 nm. The light sensor 35 is arranged in this embodiment for measuring radiation a wavelength of 400-430 nm.

In an embodiment the light source 40 comprises (but is not restricted to) 1 to 15 light emitting diodes (LEDs) with a spectral range from 360 to 390 nm (in an embodiment with emission maximum at 380 nm); The geometry of the light source can be a lineal, square or preferably a circular array of LEDs.

In an embodiment the radiation source comprises a band pass filter with a spectral range from 350 to 400 nm. Such a filter is advantageously suitable when the signalling group split of by thrombin is aminomethylcoumarine. Other filters may be needed with other signalling groups. Such a filter can also be positioned in the pathway of the rays 38,39 downstream from the source 40 and upstream from the sample support 1.

In an embodiment a diffuser is positioned in the pathway of the radiation emitted from the radiation source onto the sample to achieve homogeneous light distribution from the light source.

In an embodiment the device 30 and in particular the housing of the light tight box 32 has a insertion opening 45 for inserting the sample support 1. This will allow to insert part of the sample support 1 into the light tight box. In FIG. 2 the sample support is shown just outside the opening 45. The size of the opening 45 corresponds with the size of the support 1. In an embodiment the opening 45 and the support 1 have light sealing elements for creating a light tight seal when the support is inserted.

The opening 45 is positioned in the front panel 33 in order to direct the sample support 1. In FIG. 2 a dotted line indicates the position of the reading area 8 having strips 12,13 when the support 1 is inserted completely into the opening. The support 1 is held in a receiving space 46. In an embodiment the receiving space 46 is positioned in the cartridge retainer 34 which also forms a bottom part of the light tight box 32. However it will be clear that other embodiments are possible.

In an embodiment the housing, the cartridge retainer 34 comprises a heating block 47 for maintaining a temperature of generally 37° C., in embodiment 37° C.±0.1° C.;. This will allow maintaining the optimal temperature for the enzymatic reaction. In an embodiment, the heating block 47 serves as the "floor" for the cartridge.

The device 30 allows to monitor the fluorescence intensity in the plasma and to derive the development and disappearance of the thrombin in the plasma from said measured fluorescence. Thrombin generation can triggered in a blood sample in the presence of a fluorogenic thrombin-substrate, according to procedures known to the art.

By the action of the formed thrombin, the fluorogenic substrate is cleaved yielding as one of the products a fluorophore, which under excitation by light of the appropriate wavelength will emit light at a higher wavelength. The change of intensity of the emitted light as a function of time can be followed by means of any light-sensitive device 35, i.e. (but not restricted to) photodiodes, photomultipliers, photon detection units, and CCD sensors (preferably a monochrome CCD Firewire camera fitted with a variable focus and aperture lens).

In an embodiment the device 30 can be connected to a data processor such as a processor in a desktop computer. The camera can be connected to a desktop or laptop computer using a suitable interface. In an embodiment the interface comprises a framegrabber, USB port or Rewire port. Data acquisition can be done through the use of dedicated software while data processing can be performed either through a dedicated software or manually in a spreadsheet in order to obtain the parameters of the thrombin generation curve.

In an embodiment, the sample support or cartridge 1 is located half inside, half outside the measuring chamber. The blood is applied on the part outside, the measurement is carried out on the part inside.

In an embodiment the device 30 comprises a release mechanism for releasing the sample support 1 from the receiving opening 45. This can be a suitable locking and clicking system or a push-and-unlock system. The skilled person will be familiar with different embodiments for such a hold and release mechanism.

In an embodiment a further sensor is present in the device 30 for sensing the presence of the sample support and in a particular a suitable sample support 1. Only if a registered sample support 1 is inserted into the receiving opening 45 will the device 30 function correctly and will it perform its measurements. Sample support 1 can be provided with a suitable identification unit. Further the additional sensor can be arranged to sense whether the reading are 8 is positioned correctly and/or whether the support 1 is positioned correctly. Further the sensor can determine when a sample has reached the reading area 8 in order to start the measurement with device 30.

EXAMPLES

Example 1

Calibrator

In order to evaluate the reproducibility of the method of the invention, we used the Staphylocoagulase-Prothrombin (SCPT) complex as source of a known thrombin-like catalytic activity [4,5]. The complex was previously calibrated against human thrombin using the chromogenic substrate S-2238.

Experimental conditions: 30 μL whole citrated blood, 33 μL buffer (5% BSA, 20 mM Hepes, 140 mM NaCl, pH 7.35), and 17 μL of 2.5 mM ZGGR-AMC were incubated for 5 minutes at 37° C. At the end of the incubation, the reaction was started by addition of 20 μL of 730 nM SCPT and immediately, 80 μL of the mixture were transferred to the separator cartridge. The course of the generation of the fluorophore AMC was followed for 45 minutes. The temperature of the cartridge was kept at 37° C. As shown in the table below, the fluorescence intensity in time using the method according to the invention is highly reproducible.

The mean value, SD, SE and CV for the initial rate (the slope from 0 to 3 min), obtained from 24 consecutive experiments as described above and performed in three different days, using whole blood from three different normal donors were as follows:

| Mean slope (AU/min) | SD | SE | CV % |
|---|---|---|---|
| 8.74 | 0.87 | 0.18 | 0.77 |

Example 2

Thrombin Generation

Thrombin generation in a sample of whole blood was measured as follows: 30 μL whole citrated blood, 27 μL buffer (5% BSA, 20 mM Hepes, 140 mM NaCl, pH 7.35), and 23 μL of a mixture of recombinant tissue factor (TF)+synthetic phospholipids (PL) (to attain final concentration of 1 pM TF and 10 μM PL) were incubated for 5 minutes at 37° C. At the end of the incubation, the reaction was started by addition of 20 μL of a mixture of ZGGR-AMC+$CaCl_2$ to achieve a final concentration of 416 μM and 16.6 mM, respectively. Immediately, 80 μL of the mixture were transferred to the separator cartridge. The course of the generation of the fluorophore AMC was followed for 45 minutes. The temperature of the cartridge was kept at 37° C.

FIG. 3 shows the progress curve [A] for the apparition of the product, after correcting for substrate consumption (inner filter effect, if present at all, is negligible due to the measurement being done in a thin layer). The actual curve for the activity of free thrombin is shown in [C], and obtained from subtracting the activity due to the α2M-thrombin complex [B] from the total activity [A]. The first derivative of [C], shown in [D], represents the well known course of thrombin generation in plasma. The curve in [C] can be converted to Thrombin units using the initial rate and known activity of the calibrator. This external calibration can be done before, in parallel, or after assaying the experimental sample. Calculation of other parameters of the thrombin generation process like the Endogenous Thrombin Potential (ETP) can be done by the use of mathematical procedures known to any skilled operator [6].

In both cases the course of the generation of the fluorophore AMC was followed for 45 minutes. The temperature of the cartridge was kept at 37° C.

CITED REFERENCES

1. Turecek P L, Varadi K, Keil B, Négrier C, Berntorp E, Astermark J, Bordet J C, Morfini M, Linari S, Schwarz H P. Factor VIII inhibitor-bypassing agents act by inducing thrombin generation and can be monitored by a thrombin generation assay. *Pathophysiol Haemost Thromb* 2003; 33:16-22.
2. Varadi K, Négrier C, Berntorp E, Astermark J, Bordet J C, Morfini M, Linari S, Schwarz H P, Turecek P L. Monitoring the bioavailability of FEIBA with a thrombin generation assay. *J Thromb Haemost* 2003; 1:2374-80.
3. Hemker H C, Giesen P, Al Dieri R, Regnault V, De Smedt E, Wagenvoord R, Lecompte T, Béguin S. Calibrated automated thrombin generation measurement in clotting plasma. *Pathophysiol Haemost Thromb* 2003; 33:4-15.

4. Hendrix H, Lindhout T, Mertens K, Engels W, Hemker HC. Activation of human prothrombin by stoichiometric levels of staphylocoagulase. *J Biol Chem* 1983; 258:3637-44.
5. Bas B M, Muller A D, Hemker H C. Purification and properties of staphylocoagulase. *Biochim Biophys Acta* 1975; 379:164-71.
6. Hemker H C, Béguin S. Thrombin generation in plasma: its assessment via the endogenous thrombin potential [published erratum appears in Thromb Haemost 1995 November; 74(5):1388]. *Thromb Haemost* 1995; 74:134-8.

The invention claimed is:

1. A method for measuring thrombin generation in a whole blood sample in an assembly that comprises a sample support and a device for measuring thrombin generation in blood plasma, the method comprising:
    (a) placing the whole blood sample on the sample support which comprises a longitudinal separator medium that has a first end and a second end and comprises:
        (i) a sampling area at the first end at which the whole blood sample is deposited, and
        (ii) a reading area at the second end, said second end being receivable in an insertion opening, and a receiving space for a sample support, which separator medium allows flow migration of blood plasma while retaining blood cells,
    (b) before or after step (c), adding a fluorogenic thrombin substrate to the blood sample;
    (c) triggering thrombin generation;
    (d) prior to initiation of blood coagulation, separating blood cells from plasma in the separator medium, and
    (e) measuring the thrombin generated from the fluorogenic thrombin substrate using said device,
    wherein the device comprises:
        (i) a housing comprising a light tight box that comprises a cartridge retainer received therein;
        (ii) a light source; and
        (iii) a light sensor;
        wherein
            (A) disposed in said light-tight box are the insertion opening for inserting the sample support and for directing the sample support into the receiving space for the sample support in the cartridge retainer, and
            (B) at least part of the light source and part of the light sensor are directed towards said cartridge retainer.

2. The method according to claim 1, wherein the fluorogenic thrombin substrate comprises aminomethylcoumarine.

3. The method according to claim 1, with the proviso that the whole blood sample is not centrifuged.

4. The method according to claim 1, wherein the fluorogenic thrombin substrate comprises rhodamine-110.

5. The method according to claim 1 wherein the substrate is added before the triggering step (c).

6. The method according to claim 1 wherein the substrate is added after the triggering step (c).

7. The method according to claim 1, wherein separating step (d) is performed within about 5 to 15 seconds of step (b).

8. The method according to claim 1 wherein the separating in step (d) occurs within about 10 seconds of step (b).

9. The method according to claim 1 wherein the placing of the blood sample of step (a) occurs outside the light-tight box and the measuring is performed inside the light-tight box.

10. The method according to claim 1, wherein the separator medium further comprises one or more reagents for measuring thrombin generation.

11. The method according to claim 1, wherein the separator medium is made of cellulose or a cellulose derivative.

12. The method according to claim 1, wherein the separator medium is a membrane type FR-2 (0.7).

13. The method according to claim 1, wherein the light source is arranged to emit light with a spectral range from 350 to 400 nm and the light sensor is a camera comprising a cutoff filter with a spectral range from 400 to 430 nm.

14. The method according to claim 1, wherein the assembly further comprises a heating block that maintains a temperature in the range of about 34° C. to about 40° C.

15. The method according to claim 14, wherein the heating block maintains a temperature in the range of about 37° C. to about 38° C.

16. The method according to claim 15, wherein the heating block maintains a temperature in the range of about 37.4° C. to about 37.6° C.

* * * * *